US00PP30716P3

(12) United States Plant Patent
Post

(10) Patent No.: US PP30,716 P3
(45) Date of Patent: Jul. 16, 2019

(54) ***CHRYSANTHEMUM* PLANT NAMED 'DLFZON1'**

(50) Latin Name: ***Chrysanthemum* X *morifolium***
Varietal Denomination: DLFZON1

(71) Applicant: Arie Gerard Post, Delft (NL)

(72) Inventor: Arie Gerard Post, Delft (NL)

(73) Assignee: Deliflor Royalties B.V., Maasdijk (NL)

( * ) Notice: Subject to any disclaimer, the term of this patent is extended or adjusted under 35 U.S.C. 154(b) by 0 days.

(21) Appl. No.: 15/932,785

(22) Filed: Apr. 23, 2018

(65) Prior Publication Data

US 2018/0325005 P1 Nov. 8, 2018

Related U.S. Application Data

(60) Provisional application No. 62/602,772, filed on May 5, 2017.

(51) Int. Cl.
*A01H 5/02* (2018.01)
*A01H 6/14* (2018.01)

(52) U.S. Cl.
USPC ..... Plt./288
CPC ..... *A01H 6/1424* (2018.05)

(58) Field of Classification Search
USPC ..... Plt./288
CPC ..... A01H 5/0255
See application file for complete search history.

*Primary Examiner* — Kent L Bell
(74) *Attorney, Agent, or Firm* — C. A. Whealy

(57) ABSTRACT

A new and distinct cultivar of *Chrysanthemum* plant named 'DLFZON1', characterized by its strong and upright flowering stems; vigorous growth habit; dark green-colored leaves; relatively short response time; pompon inflorescences with white-colored ray florets; and good postproduction longevity.

2 Drawing Sheets

Botanical designation: *Chrysanthemum* X *morifolium*.
Cultivar denomination: 'DLFZON1'.

BACKGROUND OF THE INVENTION

The present invention relates to a new and distinct cultivar of *Chrysanthemum* plant, botanically known as *Chrysanthemum* X *morifolium*, commercially grown as a cut flower and hereinafter referred to by the name 'DLFZON1'.

The new *Chrysanthemum* plant is a product of a planned breeding program conducted by the Inventor in Maasdijk, The Netherlands. The objective of the breeding program is to create new freely-flowering cut *Chrysanthemum* plants with pompon inflorescences, strong flowering stems and excellent postproduction longevity.

The new *Chrysanthemum* plant originated from a cross-pollination made by the Inventor in Maasdijk, The Netherlands in March, 2013, of a proprietary selection of *Chrysanthemum* X *morifolium* identified as code designation DB 44792, not patented, as the female, or seed, parent with a proprietary selection of *Chrysanthemum* X *morifolium* identified as code designation DB 43726, not patented, as the male, or pollen, parent. The new *Chrysanthemum* plant was discovered and selected by the Inventor as a single flowering plant from within the progeny of the stated cross-pollination in a controlled greenhouse environment in Maasdijk, The Netherlands in September, 2013.

Asexual reproduction of the new *Chrysanthemum* plant by terminal vegetative cuttings in a controlled greenhouse environment in Maasdijk, The Netherlands since September, 2013 has shown that the unique features of this new *Chrysanthemum* plant are stable and reproduced true to type in successive generations.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'DLFZON1'. These characteristics in combination distinguish 'DLFZON1' as a new and distinct *Chrysanthemum* plant:

1. Strong and upright flowering stems.
2. Vigorous growth habit.
3. Dark green-colored leaves.
4. Relatively short response time.
5. Pompon inflorescences with white-colored ray florets.
6. Good postproduction longevity; plants maintain good substance for about two weeks in an interior environment.

Plants of the new *Chrysanthemum* differ from plants of the female parent selection in the following characteristics:

1. Plants of the new *Chrysanthemum* and the female parent selection differ in ray floret color as plants of the female parent selection have yellow-colored ray florets.
2. Plants of the new *Chrysanthemum* are not as resistant to *Chrysanthemum* White Rust as plants of the female parent selection.

Plants of the new *Chrysanthemum* differ from plants of the male parent selection in the following characteristics:

1. Plants of the new *Chrysanthemum* and the male parent selection differ in ray floret color as plants of the male parent selection have light purple-colored ray florets.
2. Plants of the new *Chrysanthemum* are not as resistant to *Chrysanthemum* White Rust (*Puccinia horiana*) as plants of the male parent selection.

Plants of the new *Chrysanthemum* can be compared to plants of *Chrysanthemum* X *morifolium* 'DLFHAL11', not patented. In side-by-side comparisons plants of the new *Chrysanthemum* differ from plants of 'DLFHAL11' in the following characteristics:

1. Plants of the new *Chrysanthemum* have smaller inflorescences and shorter ray florets than plants of 'DLFHAL11'.
2. Plants of the new *Chrysanthemum* are not as resistant to *Chrysanthemum* White Rust as plants of 'DLFHAL11'.

BRIEF DESCRIPTION OF THE PHOTOGRAPHS

The accompanying colored photographs illustrate the overall appearance of the new *Chrysanthemum* plant showing the colors as true as it is reasonably possible to obtain in colored reproductions of this type. Colors in the photographs may differ slightly from the color values cited in the detailed botanical description which accurately describe the colors of the new *Chrysanthemum plant.*

The photograph on the first sheet comprises a side perspective view of a typical flowering stem of 'DLFZON1' grown as a disbud-type.

The photograph on the second sheet comprises close-up views of the lower (top of the photographic sheet) and upper surfaces (bottom of the photographic sheet) of typical inflorescences and leaves of 'DLFZON1'.

DETAILED BOTANICAL DESCRIPTION

The aforementioned photographs and following observations and measurements describe plants grown during the winter in ground beds in a glass-covered greenhouse in Maasdijk, The Netherlands and under cultural practices typical of commercial cut *Chrysanthemum* production. Plants were initially given long day/short night treatments followed by short day/long night treatments to induce flower initiation and development. During the production of the plants, day temperatures ranged from 18° C. to 22° C., night temperatures ranged from 19° C. to 21° C. and light levels averaged 8 klux. Plants were nine weeks old when the photographs and the description were taken. In the following description, color references are made to The Royal Horticultural Society Colour Chart, 2015 Edition, except where general terms of ordinary dictionary significance are used.

Botanical classification: *Chrysanthemum* X *morifolium* 'DLFZON1'.

Parentage:

*Female, or seed, parent.*—Proprietary selection of *Chrysanthemum* X *morifolium* identified as code designation DB 44792, not patented.

*Male, or pollen, parent.*—Proprietary selection of *Chrysanthemum* X *morifolium* identified as code designation DB 43726, not patented.

Propagation:

*Type.*—Terminal vegetative cuttings.

*Time to initiate roots, summer.*—About six days at temperatures about 24° C.

*Time to initiate roots, winter.*—About eight days at temperatures about 22° C.

*Time to produce a rooted young plant, summer.*—About twelve days at temperatures about 24° C.

*Time to produce a rooted young plant, winter.*—About two weeks at temperatures about 22° C.

*Root description.*—Fine, fibrous; typically cream in color, actual color of the roots is dependent on substrate composition, water quality, fertilizers, substrate temperature and physiological age of roots.

*Rooting habit.*—Freely branching, medium density.

Plant description:

*Plant and growth habit.*—Herbaceous pompon cut flower that is typically grown as a disbud-type; upright plant habit; vigorous growth habit and rapid growth rate.

*Plant height, soil level to top of foliar plane.*—About 70 cm.

*Plant height, soil level to top of flower plane.*—About 75 cm.

*Plant (disbud) diameter.*—About 21.3 cm.

*Flowering stem length.*—About 50.2 cm.

*Flowering stem diameter.*—About 7 mm.

*Flowering stem internode length.*—About 2.1 cm.

*Flowering stem strength.*—Strong.

*Flowering stem aspect.*—Erect.

*Flowering stem texture and luster.*—Densely pubescent; moderately glossy.

*Flowering stem color, developing.*—Close to 145A.

*Flowering stem color, developed.*—Close to 143B to 143C.

*Leaf description.*—Arrangement: Alternate; simple. Length: About 9.6 cm. Width: About 7.6 cm. Shape: Ovate. Apex: Short apiculate. Base: Attenuate. Margin: Palmately lobed, coarsely crenate; sinuses convergent and medium-deep in depth. Texture and luster, upper surface: Densely pubescent, not rugose; moderately velvety; slightly velvety. Texture and luster, upper surface: Densely pubescent, prominent venation; slightly velvety; matte. Venation pattern: Pinnate, reticulate. Color: Developing leaves, upper surface: Close to between 137D and 138A. Developing leaves, lower surface: Close to 138B. Fully developed leaves, upper surface: Darker than between 139A and N189A; venation, close to 143B to 143C. Fully developed leaves, lower surface: Close to 147B; venation, close to 143A. Petioles: Length: About 2.3 cm. Diameter: About 2.5 mm by 3 mm. Strength: Moderately strong. Texture and luster, upper and lower surfaces: Moderately to densely pubescent; slightly glossy. Color, upper and lower surfaces: Close to 146B. Stipules: Quantity and appearance: Two leafy stipules, opposite, at the petiole attachment to the stem. Length: About 1 cm. Width: About 1.3 cm. Shape: Roughly flabellate. Texture and luster, upper and lower surfaces: Densely pubescent; matte. Color, upper surface: Darker than between 139A and N189A. Color, lower surface: Close to 147B.

Inflorescence description:

*Appearance.*—Pompon inflorescence form with obovate-shaped ray florets and tubular disc florets; inflorescences borne perpendicular to peduncles and face upright; ray and disc florets develop acropetally on a capitulum.

*Fragrance.*—Faintly fragrant.

*Flowering response.*—Under natural conditions, plant flower in the autumn/winter in the Northern Hemisphere; at other times of the year, inflorescence initiation and development can be induced under short day/long night conditions (at least 13.5 hours of darkness); uniform flowering habit and short response time, plants exposed to two weeks of long day/short night conditions after planting followed by photoinductive short day/long night conditions flower about 52 days later when grown as a disbud-type.

*Postproduction longevity.*—Good postproduction longevity; in an interior environment, inflorescences and foliage will maintain good color and substance for about two weeks; inflorescences persistent.

*Quantity of inflorescences.*—Grown as a disbud-type, all lateral inflorescence buds are removed.

*Inflorescence size.*—Diameter: About 6.7 cm. Depth (height): About 4.6 cm. Disc diameter: About 5 mm.

*Receptacles.*—Height: About 3 mm. Diameter: About 5 mm. Shape: Flattened globular. Color: Close to 146B.

*Inflorescence buds.*—Height: About 6 mm. Diameter: About 1.2 cm. Shape: Flattened globular. Texture and luster: Sparsely pubescent; slightly glossy. Color: Close to between 143B and 145B; towards the apex, close to 145A to 145B.

*Ray florets.*—Quantity and arrangement: About 250 arranged in about eight whorls. Length: About 2.7 cm. Width: About 8 mm. Shape: Obovate, strongly concave and moderately carinate. Apex: Retuse to shallowly cleft. Base: Attenuate. Margin; Entire; slightly undulate. Aspect: Initially upright to horizontal to about −20° from horizontal. Texture and luster, upper surface: Smooth, glabrous; moderately velvety; matte. Texture and luster, lower surface: Smooth, glabrous; moderately velvety; slightly glossy. Color: When opening, upper surface: Close to NN155B; apex tinged with close to 145D. When opening, lower surface: Close to NN155C; apex, close to 145D. Fully opened, upper surface: Close to NN155D; venation, close to NN155D; color does not change with development. Fully opened, lower surface: Close to NN155C; towards the apex, slightly tinged with close to 145D; venation, similar to lamina color; color does not change with development.

*Disc florets.*—Quantity and arrangement: About 15 spirally arranged in about three whorls at the center of the receptacle. Length: About 8 mm. Diameter: About 2 mm. Shape: Lower 85% fused into a tube; upper 15% free. Apex: Acute. Margin: Entire. Texture and luster, inner and outer surfaces: Smooth, glabrous; glossy. Color, when opening, inner and outer surfaces: Apex: Close to 1B. Mid-section and base: Close to 150C. Color, fully opened, inner and outer surfaces: Apex: Close to 5B. Mid-section and base: Close to 145C.

*Involucral bracts.*—Quantity and arrangement: About 30 arranged in three whorls. Length: About 1 cm. Width: About 4 mm. Shape: Ovate. Apex: Obtuse. Base: Cuneate. Margin: Entire. Texture and luster, upper surface: Smooth, glabrous; glossy. Texture and luster, lower surface: Sparsely pubescent; slightly glossy. Color, upper surface: Close to 144A; margins, translucent, and close to 157D; apex, close to 157D. Color, lower surface: Close to 143A; margins, translucent, close to 157D; apex, close to N199A.

*Peduncles* (*if grown as a spray-type*).—Length, terminal peduncle: About 1.4 cm. Diameter, terminal peduncle: About 4 mm. Length, third peduncle: About 1 cm. Diameter, third peduncle: About 3 mm. Strength: Strong. Aspect, terminal peduncle: Mostly upright. Aspect, third peduncle: About 45° from the flowering stem axis. Texture and luster: Densely pubescent; matte. Color: Close to 143B to 143C.

*Reproductive organs.*—Androecium: Present on disc florets only. Quantity: About five per floret. Filament length: About 3 mm. Filament color: Close to 150C. Anther size: About 0.5 mm by 2 mm. Anther shape: Narrowly oblong. Anther color: Close to 12A. Pollen amount: Scarce. Pollen color: Close to 14A to 14B. Gynoecium: Present on both ray and disc florets. Quantity: One per floret. Pistil length: About 5.5 mm. Style length: About 5 mm. Style color: Close to 150B. Stigma diameter: About 1.5 mm. Stigma shape: Three-parted, decurrent. Stigma color: Close to 13A to 13B. Ovary color: Close to 145D.

*Seeds and fruits.*—Seed and fruit production have not been observed on plants of the new *Chrysanthemum* to date.

Disease & pest resistance: Resistance to pathogens and pests common to *Chrysanthemum* plants has not been observed on plants of the new *Chrysanthemum* grown under commercial conditions.

Temperature tolerance: Plants of the new *Chrysanthemum* have been observed to tolerate temperatures ranging from about −12° C. to 35° C.

It is claimed:

1. A new and distinct *Chrysanthemum* plant named 'DLFZON1' as illustrated and described.

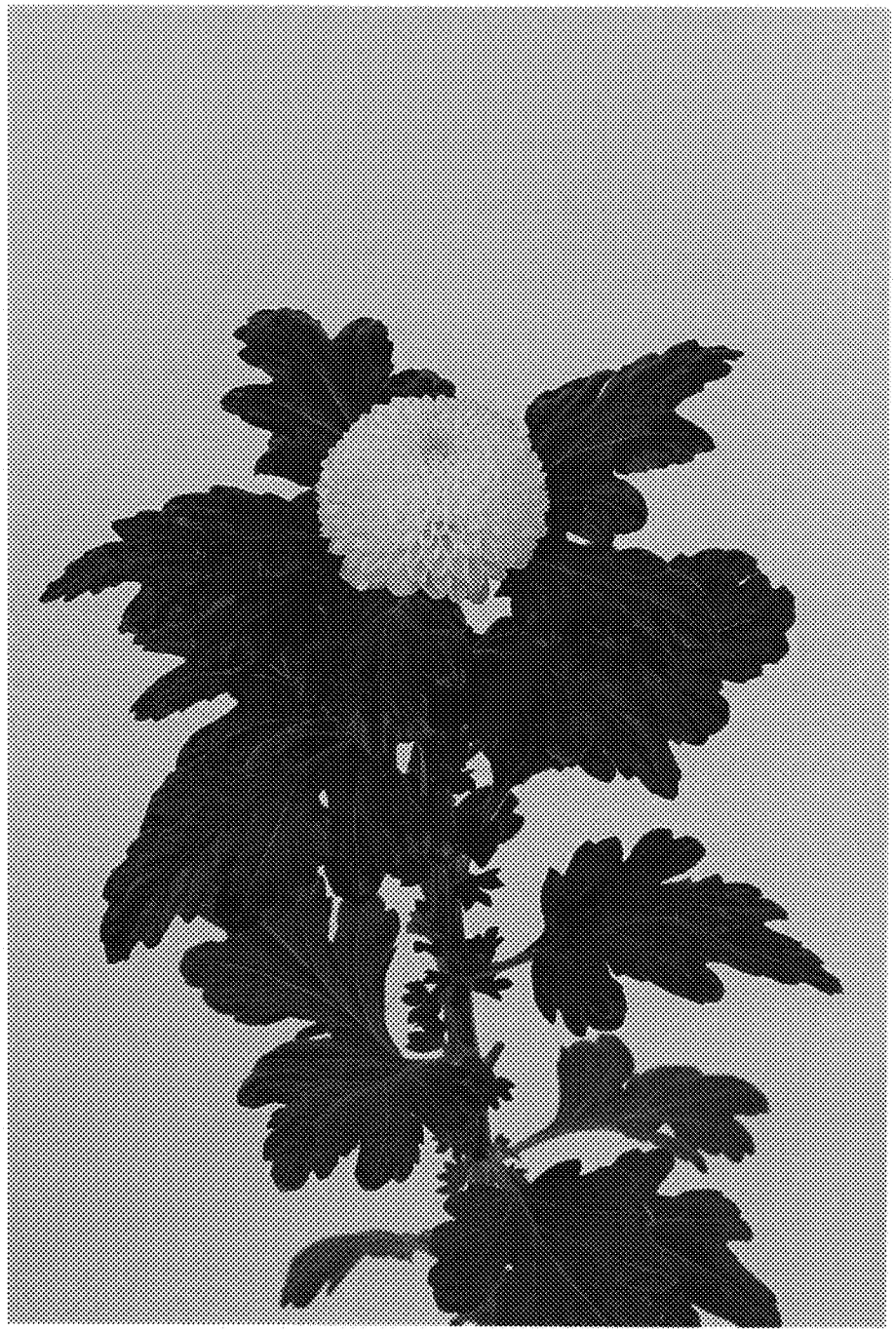

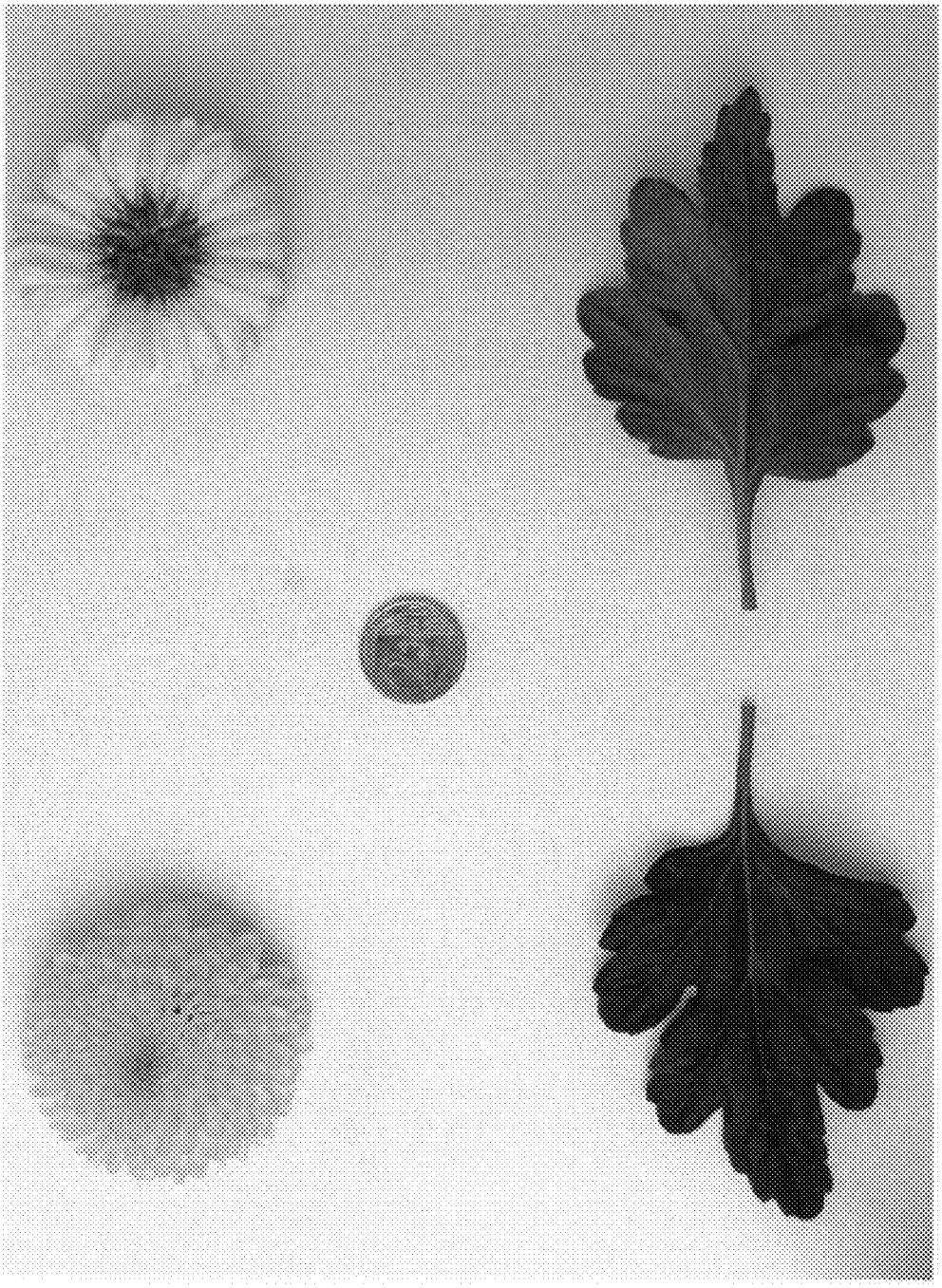

* * * * *